United States Patent
Teirstein

[11] Patent Number: 6,050,930
[45] Date of Patent: Apr. 18, 2000

[54] IRRADIATION CATHETER WITH EXPANDABLE SOURCE

[76] Inventor: Paul S. Teirstein, 402 Coast Blvd., South, La Jolla, Calif. 92037

[21] Appl. No.: 09/088,840

[22] Filed: Jun. 2, 1998

[51] Int. Cl.[7] ........................................... A61N 5/00
[52] U.S. Cl. ................................................... 600/3
[58] Field of Search ............................. 600/1–8

[56] References Cited

U.S. PATENT DOCUMENTS

| | | | |
|---|---|---|---|
| 5,213,561 | 5/1993 | Weinstein et al. | 600/7 |
| 5,302,168 | 4/1994 | Hess | 600/3 |
| 5,725,572 | 3/1998 | Lam et al. | 600/3 |
| 5,863,284 | 1/1999 | Klein | 600/3 |

Primary Examiner—Samuel G. Gilbert
Attorney, Agent, or Firm—Gerald W. Spinks

[57] ABSTRACT

A radiation delivery system having an expandable radiation source made of a pliable material. The source body is made of a material such as a foam or sponge, or a fibrous material such as the soft bristles of a pipe cleaner. The spongy or fibrous material is made radioactive by the implantation of a radioactive isotope. The radioactive isotope can be located throughout the pliable source material, or concentrated in a desired region, such as the surface or near-surface region. This compressible radioactive source material, when constrained by a constraining housing or a catheter, has a very low profile. However, when the constraining housing or catheter is withdrawn, the expandable source material expands and fills the surrounding space, such as a blood vessel lumen. In this way, the radioactivity, impregnated in the expandable source material, is brought into direct contact with the vessel wall.

22 Claims, 2 Drawing Sheets

IRRADIATION CATHETER WITH EXPANDABLE SOURCE

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention is in the field of devices used to subject portions of a blood vessel to nuclear radiation to prevent restenosis of the irradiated area after performance of an angioplasty procedure.

2. Background Information

A common problem after performance of a percutaneous transluminal coronary angioplasty is the restenosis of the treated area. In fact, restenosis occurs in 30% to 50% of cases. Restenosis occurs, at least in part, as a result of vascular smooth muscle cell migration, proliferation, and neointima formation at the site of the angioplasty. It has been shown that intracoronary delivery of ionizing radiation causes focal medial fibrosis, which when delivered at the site of the angioplasty, impedes the restenosis process. Adjacent coronary segments and the surrounding myocardium are undamaged by the irradiation treatment.

Delivery of the ionizing radiation at the site of the stenosis can be achieved by the introduction of an irradiation source, such as a ribbon, through an infusion catheter. In such systems, the infusion catheter is inserted to the site of the stenosis over a guidewire which may be inserted before, or alternatively, left after, the performance of an angioplasty procedure. After insertion of the infusion catheter, the guidewire is usually removed from the catheter, and the irradiation ribbon is inserted in its place. The irradiation ribbon typically incorporates a plurality of Iridium-192 seeds or pellets near its distal end. This plurality of radioactive sources arranged essentially in a line approximates a line source, although the intensity of the radiation will vary axially to some extent, depending upon the spacing and length of the seeds. Other sources that might not be line sources of ionizing radiation can be used, as well.

Such systems have several disadvantages. First, location of the radioactive material radially within the blood vessel is often uncontrolled. Rotation of the infusion catheter may assist in centering the radiation source within the stenosis, in some cases, but this method is not always effective. Centering of the radioactive material within the tissues injured by the angioplasty may be required, because it is important to deliver a known dose of radiation uniformly to the affected tissue. The intensity of gamma or beta radiation emanating from a source varies inversely with the square of the radial distance from the source. Therefore, if the radiation source is not centered within the blood vessel, the dose delivered to one side of the vessel can vary greatly from the dose delivered to the opposite side. In addition, if the line source lies at an angle to the centerline of the vessel, rather than being concentric therewith, or at least parallel thereto, the dose delivered can vary axially by an appreciable amount, throughout the length of the stenosis.

A second disadvantage of known systems is that dosimetry is often inaccurate. Proper dosimetry is essential for effective treatment of vascular disease with radiation therapy. There are two general classifications of radiation sources used in these applications, gamma and beta. Gamma radiation is highly penetrating and can act at a relatively far distance from the source. Beta radiation, however, penetrates very weakly and will only adequately treat tissue approximately 2 or 3 mm. away from the source. Beta radiation is also easily shielded by metals and thick plastics. One of the advantages of beta radiation over gamma radiation is less general radiation exposure to the patient and attending health care personnel. The disadvantage of beta radiation is the difficulty in getting an adequate dose delivered to the intended target, because the dose drops off so quickly with distance. The advantages of gamma radiation are excellent penetration, providing favorable dosimetry. The disadvantages of gamma radiation are increased exposure to the patient and the hospital personnel.

Animal and human studies have shown that a dose of approximately 800 to 3000 cGy will be effective at inhibiting the proliferation of vascular disease. The challenge is delivering this dose to the vessel wall segments responsible for the proliferation process, without delivering too high a dose to the innermost layers of the vessel wall. Too high a dose delivered to the inner layers of the vessel wall could create a weakening of the wall, leading to perforation and/or accelerated disease.

Recently, excellent dosimetry to treat vascular disease has been demonstrated using a radioactive liquid filled balloon. Radioactive isotopes such as Re-188 penetrate approximately 3 mm. from the source. When delivered through a liquid filled balloon system, the radioactive isotope is mixed in the balloon and is held up against the vessel wall by the balloon. Therefore, the radioactive isotope is brought to the vessel wall so that its approximate 3 mm. penetration is from the edge of the balloon catheter. This has advantages over the more traditional wire-based beta sources where the approximate 3 mm. penetration is measured from a wire located within a delivery catheter, which is placed at or near the center of the vessel lumen. Additionally, since the radioactive source is mixed homogeneously in the balloon, the vessel is, in essence, exposed to multiple radioactive sources distributed throughout the balloon, some directly against the vessel wall and others more toward the center of the vessel.

One of the disadvantages of a liquid filled balloon is that the balloon will always have a finite rate of breakage. A broken balloon will lead to radioactive materials contaminating the human circulatory system which could have adverse, unwanted side effects. Furthermore, when the balloon is deflated, most of the radioactivity is withdrawn into a shielded housing, such as a large syringe or bladder; however, some small amount of radioactivity remains within the balloon and in the catheter connecting the balloon to the shielded storage housing. The physician/operator must remove the balloon catheter from the patient's body, which will, of necessity, require placing his or her hands on the catheter. Though the catheter contains only a small amount of radioactivity, there is a potential for unwanted operator exposure. Finally, some liquid filled balloon catheter systems require the operator to fill and prepare the balloon in the cardiac catheterization laboratory. This opens the possibility of contamination due to unintentional spillage by the operator, as the system is prepared and filled.

It is an object of the present invention to provide a catheter assembly for irradiation of a stenotic segment of a blood vessel, which can place an expandable irradiation source at a desired location within a blood vessel, and expand the source to contact, or nearly contact, the blood vessel wall. It is a further object of the present invention to provide an irradiation catheter assembly with an expandable source, which avoids the risk of releasing radiation into the bloodstream, which minimizes operator exposure, and which avoids the risk of contamination of the catheterization laboratory. Finally, it is an object of the present invention to provide a catheter assembly which is economical to manufacture and easy to use.

BRIEF SUMMARY OF THE INVENTION

The present invention comprises a new radiation delivery system that has the benefits of the liquid filled balloon, without the disadvantages. The irradiation source used in the present invention is a novel expandable source body made of a pliable material. This constitutes a "spongy" material such as a foam or sponge, or a fibrous material such as the soft bristles of a pipe cleaner. Either of these types of material result in an expandable source body which is substantially solid, in other words not hollow and not liquid. The term "substantially" solid is used here because, of course, numerous cavities or spaces are present within either the spongy material or the fibrous material. In either case, the spongy or fibrous material is made radioactive with known techniques such as ion implantation. The radioactive isotope can be located throughout the pliable source material, or concentrated in a desired region, such as the surface or near-surface region. A protective membrane can be formed surrounding the pliable source material.

This compressible radioactive source material, when constrained by a constraining housing such as a tube or a delivery catheter, has a very low profile. However, when the constraining housing is withdrawn, the expandable source material expands and fills the surrounding space, such as a blood vessel lumen. In this way, the radioactivity, impregnated in the expandable source material, is brought into direct contact with the vessel wall. If desired, a bypass channel can provide a flow path past the expanded source, to allow blood to flow through the blood vessel during irradiation. For example, the bypass channel can pass through the source material. This will allow for blood to flow through the expandable source material, allowing perfusion of the heart muscle during radiation exposure, but still yielding improved dosimetry over that of a wire source by bringing the radioactive material closer to the vessel wall.

Alternatively, the source material can be constructed so that its greatest degree of expansion is limited, so that the pliable material expands until it is close to the vessel wall, but does not actually contact it. This will allow for blood to flow around the perimeter of the expanded source material.

With the radioactive material located throughout the pliable material, the dosimetry approximates that of a liquid filled balloon, where the radiation emanates from a continuous cross section of points throughout the blood vessel. With the radioactive material localized along or near the outer surface of the pliable material, in its expanded state, this device will behave more like a radioactive stent, with the radiation emanating almost entirely from the points directly against or near the blood vessel wall. These alternatives provide a great deal of flexibility for dosimetry.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
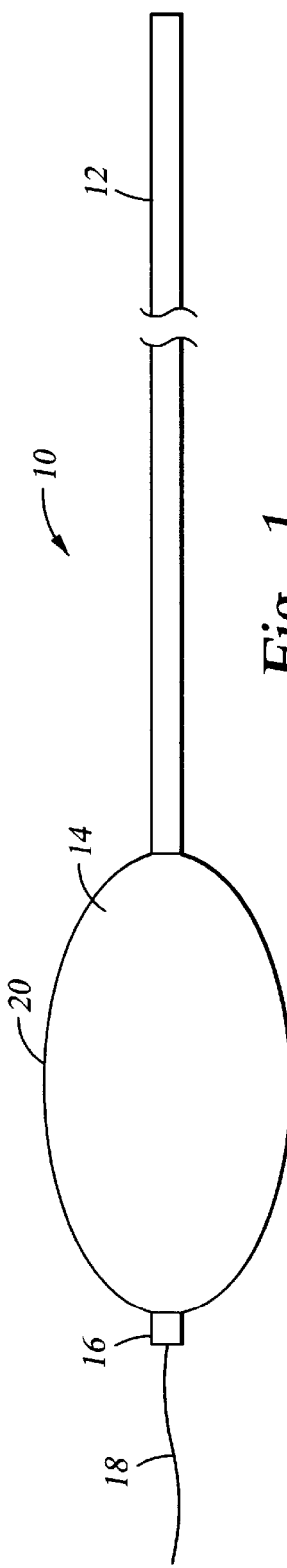
FIG. 1 is an elevation view of a radiation delivery device according to the present invention.

As shown in FIG. 1, a radiation delivery device 10 according to the present invention includes a pusher element 12 which has mounted at or near its distal tip 16 a pliable, expandable source body 14. Here, the source body 14 is shown in its fully expanded state. It is desirable to have a guidewire 18 extending beyond the distal tip 16 of this device 10 so that it can be more easily inserted into a coronary artery. The guidewire 18 can be simply a segment of floppy wire extending only from the tip of the pusher element, to facilitate insertion of the device 10 without use of a separate guidewire. Alternatively, in some embodiments of the device 10, the guidewire 18 can be a conventional guidewire over which the device 10 is inserted into the coronary artery. Either way, the use of the guidewire 18 protects the vessel wall from damage resulting from scraping by the expandable source body 14 or the pusher element 12 to which the expandable source body 14 is mounted.

The pusher element 12 comprises a flexible elongated wire or plastic element which is sufficiently stiff to insert the device 10 into a coronary artery. The pusher element 12 can be either a solid elongated filament, or cable constructed of filaments, or it can be a hollow elongated tube, such as a catheter or hypo-tube. If the pusher element 12 is at least partially tubular, it can be used with a conventional guidewire as discussed above.

The pliable source body 14 is constructed largely of a foam or spongy material, or a soft mass of fiber, much like the bristles of a pipe cleaner. This allows the source body 14 to be compressed for insertion into an artery, followed by expansion in the area of the lesion for administration of a dose of radiation. The source body 14 can be sized to expand until it contacts the walls of the blood vessel, or it can be sized to stop its expansion at a smaller diameter, leaving a blood flow path around the perimeter of the expanded source body 14. This allows blood flow to continue perfusion of the distal heart tissue during administration of the radiation source. The pliable material of the source body 14 is made radioactive by known techniques such as ion implantation. It can also be desirable to encapsulate the pliable material of the source body 14 within an expandable protective membrane 20 which will ensure the integrity of the radioactive foam or fibers, making sure that pieces of the pliable material do not break off and enter the blood stream. The protective membrane 20 will also shield the pliable source material from blood products contamination. It is in most instances desirable, though not essential, that the pliable source material not come in contact with blood, because the blood could leach off the radioactive material into the blood stream.

Figure 2:
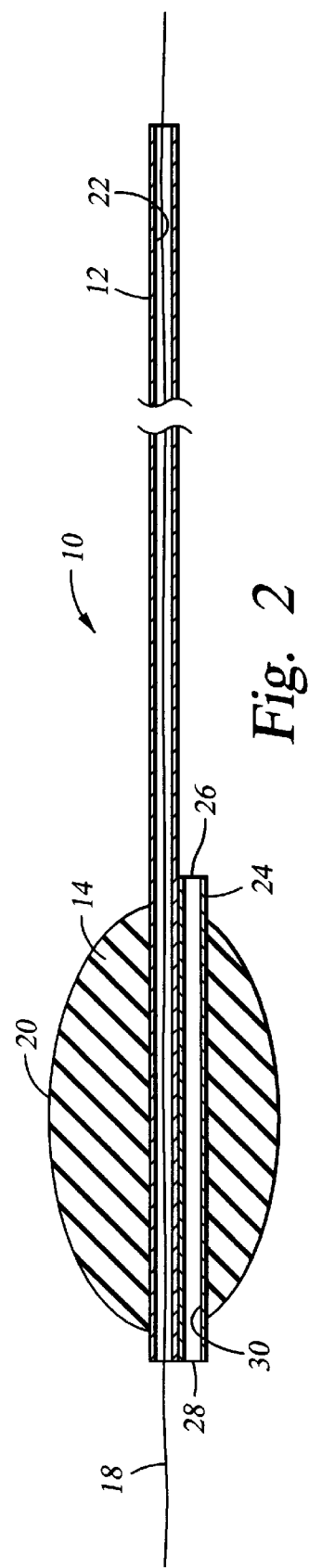
FIG. 2 is a longitudinal section view of a first embodiment of the radiation delivery device shown in FIG. 1.

In FIG. 2, a longitudinal section view of one embodiment of the radiation delivery device 10 is shown. In this embodiment, the pusher element 12 is a hollow elongated tube, such as a hypo-tube, with a lumen 22 through which the guidewire 18 can be passed as the device 10 is inserted into a coronary artery over the guidewire 18. This embodiment also exhibits a fluid bypass channel 24 which allows the flow of blood past the expanded source body 14, in the case where the source body 14 expands against the blood vessel wall. The bypass channel 24 can be incorporated with either the solid or the tubular pusher element 12. The bypass channel 24 in this embodiment is external to the pusher element 12, with the channel 24 passing directly through the expanded source body 14. Blood can enter a proximal port 26 proximal to the expanded source body 14, and exit a distal port 28 distal to the expanded source body 14, to perfuse the heart tissue, via the lumen 30 of the bypass channel 24, during administration of the radiation dose.

The radioactive isotope can be impregnated throughout the cross-hatched area of the source body 14, causing the pliable source body 14 to approximate the radiation delivery of a balloon filled with radioactive liquid.

Figure 3:
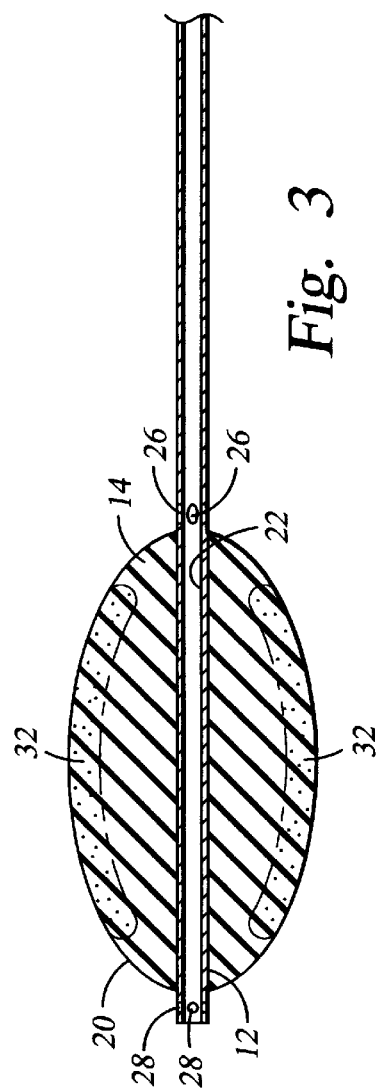
FIG. 3 is a longitudinal section view of a second embodiment of the distal portion of the radiation delivery device according to the present invention.

FIG. 3 shows a second embodiment of the distal portion of the radiation delivery device 10, which illustrates several features which can be incorporated into the device 10, or substituted for other features. In this embodiment, the distal portion of the lumen 22 of the pusher element 12 constitutes the fluid bypass channel. A plurality of proximal ports 26 allow blood to enter the pusher element lumen 22 proximal to the expanded source body 14. If needed for sufficient flow, a second plurality of distal ports 28 can be formed in the distal end 16 of the pusher element 12, to allow blood to exit the pusher element lumen 22 distal to the expanded source body 14.

FIG. 3 also illustrates that the radioactive isotope can be impregnated into the pliable source body 14 in selected areas such as the peripheral area 32 near the surface of the source body 14. Limiting the radioactive isotope to the peripheral area 32 causes the pliable source body 14 to approximate the radiation delivery of a radioactive stent, improving the penetration of the radiation into the vessel tissue by positioning the isotope at or near the vessel wall.

Figure 4:
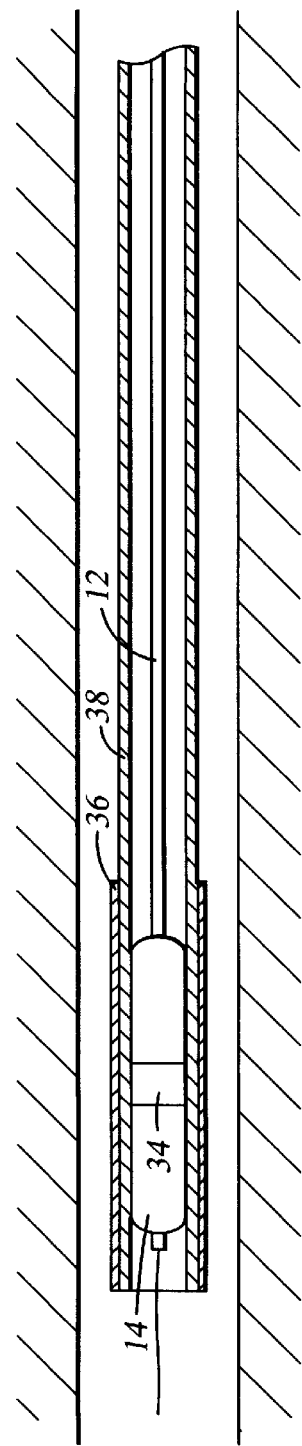
FIG. 4 is a partial longitudinal section view of a radiation delivery system according to the present invention, disposed within a blood vessel, with the pliable source body compressed within a housing, such as a delivery catheter.
Figure 5:
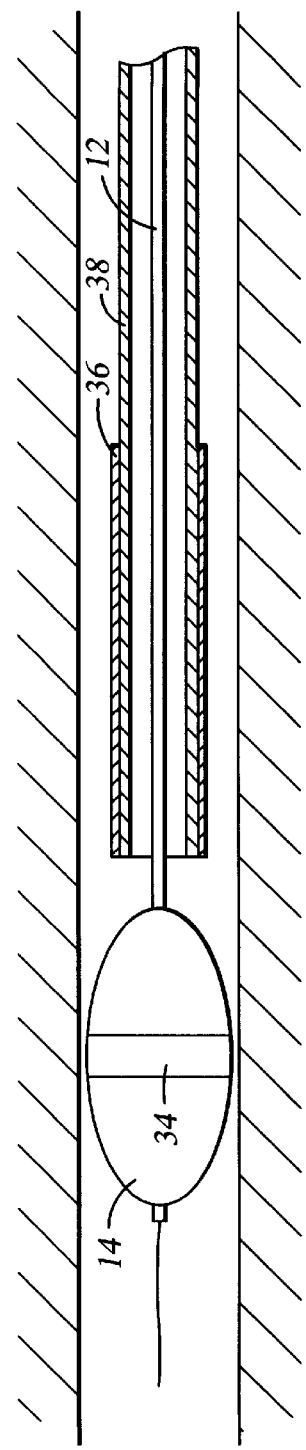
FIG. 5 is a partial longitudinal section view of the radiation delivery system shown in FIG. 4, with the housing withdrawn to allow the pliable source body to expand.

FIGS. 4 and 5 show what happens to the expandable source body 14 as it is delivered into a selected portion of the coronary artery in a compressed state within a retention housing 38, and then expanded for radiation delivery. As seen in these figures, one embodiment of the retention housing 38 for compressing and delivering the source body 14 is simply a tube, in the form of a delivery catheter, that could carry the radiation delivery device 10. Other types of housings could be used as well, with the common feature being that the housing 38 is a tube sized to compress the source body 14 to a size which will allow insertion of the source body 14 into the coronary artery to a selected site. The housing tube 38 could be long, such as the delivery catheter shown, or it could be a much shorter tube, as long as it is long enough to constrain the source body 14 to a small diameter. If a delivery catheter, as shown, is used for the retention housing 38, the delivery catheter can be inserted to the desired location over a conventional guidewire. Then, the guidewire can be withdrawn, and the radiation delivery device 10 can be inserted through the delivery catheter. Alternatively, if the tubular type of pusher element 12 is used, the pusher element 12 can be inserted through the delivery catheter over the guidewire. As still another alternative, a channel like the channel 24 could be formed on the delivery catheter and used as a guidewire channel, in which case it could be either short, as shown, in the typical fashion of a rapid exchange catheter, or it could extend up to the full length of the delivery catheter. Both of these alternatives would allow the guidewire to remain in place during radioactive source delivery. The physician would not have to remove the guidewire before placing the source.

A radiopaque marker 34 can be placed on the source body 14 to facilitate viewing of the location of the source body by the surgeon, using fluoroscopy. A radiation shield 36, which can be a plastic or metallic jacket of sufficient thickness and composition to contain the type and energy of radiation being used, can be applied to, or incorporated within, the housing 38. The radiation shield 36 can be short, as shown, just long enough to cover the radioactive source body 14, or it can extend up to the full length of the housing 38. This radiation shield 36 prevents unnecessary exposure of the patient or attending health care personnel, during insertion of the source body 14 to the desired location in the coronary artery. To further enhance viewing of the progress of the delivery catheter, a second radiopaque marker can be incorporated into the radiation shield 36, or placed elsewhere on the retention housing 38. Once delivered to the desired location, either the source body 14 is pushed out of the retention housing 38, or the retention housing 38 is pulled back from the source body 14. In either case, when the source body 14 is beyond the distal end of the retention housing 38, the source body 14 will expand. If a short tube, rather than a delivery catheter, is used for the retention housing 38, the radiation delivery device 10 and the retention housing 38 can be inserted either directly through the artery, or through a separate delivery catheter. In such cases, removal of the retention housing 38 from the source body 14 would be by some other means, such as a tether wire.

Figure 6:
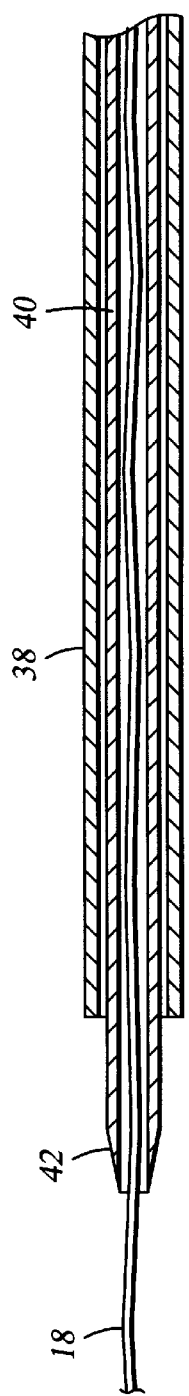
FIG. 6 is a longitudinal section view of a delivery catheter as used in the present invention, with a tapered trocar and guidewire disposed therein.

Another feature which can be incorporated into the present invention is an inner trocar 40, as shown in FIG. 6. This trocar 40 would simply be another catheter that is slightly longer than the delivery catheter, and the trocar 40 would optimally have a tapering tip 42. This would allow the delivery catheter to be placed over a guidewire, with very little "step-up" between the guidewire and the outer rim of the delivery catheter. This enhances deliverability, because the edges of the delivery catheter are less likely to catch on the blood vessel wall, or on pieces of calcium or stent struts, as the catheter is delivered to the desired location. The inner trocar 40 and the guidewire could both be removed prior to insertion of the radiation delivery device 10. Or, if the tubular type of pusher element 12 is used, the trocar 40 could be removed, leaving the guidewire 18 in place, followed by insertion of the radiation delivery device 10 over the guidewire 18. The latter method would be particularly useful if the retention housing 38 in use is a short tube, rather than a delivery catheter.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A device for disposing radioactive material at a selected position in a blood vessel, said device comprising:
   an elongated flexible pusher element;
   a self expanding body attached to said pusher element, said self expanding body being a substantially solid body composed of pliable material; and radioactive material disposed at selected locations on said self expanding body.

2. The device recited in claim 1, wherein said pusher element comprises a flexible tubular element.

3. The device recited in claim 1, further comprising a fluid bypass channel formed through said self expanding body, said bypass channel having a first port proximal to said self expanding body, and a second port distal to said self expanding body.

4. The device recited in claim 3, wherein said bypass channel passes through said pusher element.

5. The device recited in claim 3, wherein said bypass channel is external to said pusher element.

6. The device recited in claim 1, further comprising a protective membrane surrounding said self expanding body.

7. The device recited in claim 1, wherein said radioactive material is disposed substantially uniformly throughout said self expanding body.

8. The device recited in claim 1, wherein said radioactive material is predominately disposed near the surface of said self expanding body.

9. The device recited in claim 1, further comprising a radiopaque marker on said self expanding body.

10. A device for disposing radioactive material at a selected position in a blood vessel, said device comprising:
   an elongated flexible pusher element;
   an expandable body attached to said pusher element, said expandable body being a substantially solid body composed of pliable material; and
   radioactive material disposed at selected locations on said expandable body;
   wherein said expandable body comprises a mass of resilient fibrous material.

11. A device for disposing radioactive material at a selected position in a blood vessel, said device comprising:
   an elongated flexible pusher element;
   an expandable body attached to said pusher element, said expandable body being a substantially solid body composed of pliable material; and
   radioactive material disposed at selected locations on said expandable body;
   wherein said pusher element comprises a flexible solid filament.

12. A device for disposing radioactive material at a selected position in a blood vessel, said device comprising:
   an elongated flexible pusher element;
   an expandable body attached to said pusher element, said expandable body being a substantially solid body composed of pliable material;
   radioactive material disposed at selected locations on said expandable body; and
   a tubular delivery housing within which said expandable body can be selectively disposed, and from which said expandable body can be exposed.

13. The device recited in claim 12, further comprising a radiation shield on said tubular delivery housing.

14. The device recited in claim 12, wherein said tubular delivery housing comprises an elongated catheter.

15. The device recited in claim 14, further comprising a guidewire channel formed on said elongated catheter.

16. The device recited in claim 12, further comprising a radiopaque marker on said tubular delivery housing.

17. A device for disposing radioactive material at a selected position in a blood vessel, said device comprising:
   an elongated flexible pusher element;
   an expandable body attached to said pusher element, said expandable body being a substantially solid body composed of pliable material; and
   radioactive material disposed at selected locations on said expandable body;
   wherein said expandable body comprises a spongy material.

18. A system for disposing radioactive material at a selected position in a blood vessel, said device comprising:
   an elongated flexible guidewire;
   an elongated delivery catheter, said catheter being insertable into the vascular system of a patient over said guidewire;
   an elongated flexible pusher element, said pusher element being insertable through said delivery catheter;
   an expandable body attached to said pusher element, said expandable body being a substantially solid body composed of pliable material;
   radioactive material disposed at selected locations on said expandable body; and
   a radiation shield on said delivery catheter.

19. The system recited in claim 18, further comprising a guidewire channel on said delivery catheter.

20. The system recited in claim 18, further comprising a hollow flexible trocar sized to fit within said delivery catheter, said trocar having a lumen sized to receive said guidewire, said trocar having a tapered distal tip.

21. The system recited in claim 18, wherein said pusher element comprises a flexible tubular element, said pusher element having a lumen sized to receive said guidewire.

22. The system recited in claim 18, further comprising a fluid bypass channel formed through said expandable body, said bypass channel having a first port proximal to said expandable body, and a second port distal to said expandable body.

* * * * *